United States Patent [19]
Richards et al.

[11] Patent Number: 6,036,949
[45] Date of Patent: Mar. 14, 2000

[54] TREATMENT OF FIBROMYALGIA WITH LOW DOSES OF INTERFERON

[75] Inventors: Alan B. Richards, Amarillo; Edward Sherwood, Lago Vista, both of Tex.

[73] Assignee: Amarillo Biosciences, Inc., Amarillo, Tex.

[21] Appl. No.: 09/035,290

[22] Filed: Mar. 5, 1998

[51] Int. Cl.[7] .................................................. A61K 38/21
[52] U.S. Cl. .......................................... 424/85.7; 424/85.4
[58] Field of Search .................................... 424/85.4, 85.2

[56] References Cited

U.S. PATENT DOCUMENTS 4,462,985  7/1984  Cummins, Jr. .
5,019,382  5/1991  Cummins, Jr. .

OTHER PUBLICATIONS

Middleton, G.D., et al. Arthritis Rheum. 37(9 suppl.): S214, abst. No. 328, 1994.
Rivera, J., et al. Br. J. Rheum. 36(9): 981–85, 1997.
"Fibromyalgia Syndrome: A Review"; Reiffenberger, et al., American Family Physician, vol. 53, No. 5, Apr. 1996, pp. 1698–1704.
"The American College Of Rheumatology 1990 Criteria For The Classification Of Fibromyalgia", Wolfe, et al., Arthritis and Rheumatism, vol. 33, No. 2 (Feb. 1990), pp. 160–172.
"Fibromyalgia Syndrome", G.O. Littlejohn, MJA Practice Essential, vol. 165, Oct. 7, 1996, pp. 387–391.
"Fibromyalgia Syndrome: Current Concepts in Pathophysiology, Clinical Features, and Management", Robert W. Simms, Arthritis Care and Research, vol. 9, No. 4, Aug. 1996, pp. 315–328.
"Effect of an Antidiencephalon Immune Serum on Pain and Sleep in Primary Fibromyalgia", C. Kempenaers, et al., Neuropsychobiology 1994:30:66–72.
"Chlormezanone in Primary Fibromyalgia Syndrome: A Double Blind Placebo Controlled Study", M. Pattrick, et al., British Journal of Rheumatology, 1993:32:55–58.
"Effect of Zopiclone on Sleep Quality, Morning Stiffness, Widespread Tenderness and Pain and General Discomfort in Primary Fibromyalgia Patients. A Double–Blind Randomized Trial", M. Gronblad, et al., Clinical Rheumatology, 1993, 12, No. 2, pp. 186–191.
"An Analytical Review of 24 Controlled Clinical Trials for Fibromyalgia Syndrome (FMS)", White and Harth, Pain, 64 (1996) pp. 211–219.
"Comparison of Tenoxicam and Bromazepan in the Treatment of Fibromyalgia: A Randomized, Double–Blind, Placebo–controlled Trial", Carrera, et al., Pain, 65 (1996) pp. 221–225.

*Primary Examiner*—David L. Fitzgerald
*Attorney, Agent, or Firm*—Barnes & Thornburg

[57] ABSTRACT

A method is described for using interferon in the treatment of human patients afflicted with fibromyalgia to alleviate one or more symptoms associated with that disease state. Fibromyalgia positive patients treated buccally, sublingually or by oral ingestion administration of low doses of interferon enjoy a reduction in clinical symptoms of the disease.

11 Claims, No Drawings

TREATMENT OF FIBROMYALGIA WITH LOW DOSES OF INTERFERON

FIELD OF INVENTION

The present invention relates to a composition and method for treatment of patients afflicted with fibromyalgia. More particularly, this invention is directed to a composition and method for relieving symptoms associated with chronic fibromyalgia in human patients by administering low doses of interferon.

BACKGROUND AND SUMMARY OF THE INVENTION

Fibromyalgia is a common disabling disorder characterized by chronic musculoskeletal aches and pain, stiffness, general fatigue, and sleep abnormalities including diminished stage four sleep. Examination of affected patients reveals increased tenderness at muscle and tendon insertion sites, known as "tender points". Fibromyalgia patients experience severe morning stiffness and a generalized decreased of overall physical function, and they are often prone to headaches, memory and concentration problems, dizziness, numbness and tingling, and crampy abdominal or pelvic pain. Fibromyalgia affects 2–4% of the population and is most frequently found in women between 20 and 50 years old, though it can also affect men, the elderly and minors.

Diagnosis of fibromyalgia is often overlooked due to the general nature of the symptoms and the lack of diagnostic lab or x-ray abnormalities. The disorder is often concomitant with, masked by or confused with other diseases such as rheumatoid arthritis, chronic fatigue syndrome or irritable bowl syndrome. A physician can positively diagnosis fibromyalgia syndrome by finding the symptoms of generalized musculoskeletal pain and pain at more than 11 of 18 defined characteristic "tender points" when finger pressure of about 4 kg is applied to the area, which test is known as the "tender point index".

Currently the best treatment available for fibromyalgia consists of a combination of analgesics, sleep aids, exercise programs emphasizing stretching and cardiovascular fitness, relaxation techniques and other measures to reduce muscle tension, and educational programs to reduce emotional and physical stress. Numerous pharmaceutical regimes have been tried including treatment with serotonin modulators and antisera to endogenous psychoactive agents. Therapeutic response can be assessed by the reduction of pain in the tender point index and improvement in several generalized criteria such as physical function, stiffness, fatigue, depression, tenseness, etc. Responses to these various therapies have proven variable within a patient pool and have rarely exceeded modest relief of some symptoms. Often, initial therapeutic gains are temporary with the long term outcome marginally if at all distinguishable from placebo results.

There exists a significant need for more effective therapy for patients afflicted with fibromyalgia. The present invention is directed to a method for treating the disease condition (as measured by reduction of clinical symptoms) by treating a fibromyalgia afflicted patient with low doses of interferon administered either bucally, sublingually or by oral ingestion. In one embodiment a Type I interferon is administered in a solid or liquid dosage form by oral ingestion, or it is administered to the oral and pharyngeal mucosa of a patient diagnosed with fibromyalgia at a dose of about 1 to about 1500 IU interferon per day, more preferably, about 5 to about 1000 IU per day. In another embodiment interferon is administered orally in doses of about 10 to about 250 IU per day. In another embodiment, interferon administered is about 15 to about 150 IU per day. The daily doses can be divided into multiple dosages forms administered two or more times per day.

Interferon for oral ingestion administration in accordance with the present invention can be formulated using art-recognized techniques into pharmaceutically acceptable liquid carriers or in combination with pharmaceutically acceptable solid carriers in the form of tablets, capsules, caplets, or gel-seals.

Interferon for buccal or sublingual administration to the patient's oral and pharyngeal mucosa can be formulated in liquid forms or in solid forms using a saliva soluble carrier to form saliva soluble solid dosage forms which can be held in the mouth for a time sufficient to dissolve the dosage form and form an interferon-containing saliva solution in contact with the patient's oral and pharyngeal mucosa to stimulate a therapeutic effect.

DETAILED DESCRIPTION OF THE INVENTION

"Interferon" is a term generically comprehending a group of vertebrate glycoproteins and proteins which are known to have antiviral, antiproliferative and immunomodulatory activity. In the early years of interferon research, an international committee assembled to devise a system for orderly nomenclature of interferons defined "interferon" as follows: "To qualify as an interferon a factor must be a protein which exerts virus non-specific, antiviral activity at least in homologous cells through cellular metabolic process involving synthesis of both RNA and protein." *Journal of Interferon Research*, 1, pp. vi (1980). "Interferon" as used herein in describing in the present invention shall be deemed to have that definition and shall contemplate proteins, including glycoproteins, regardless of their source or method of preparation or isolation.

Interferons have generally been named in terms of the species of animal cells producing the substance, the type of cell involved (e.g., leukocyte/lymphoblastoid or fibroblast) and, occasionally, the type of inducing material responsible for the interferon production. The designations alpha ($\alpha$), beta ($\beta$) and gamma ($\gamma$) have been used to correspond to the previous designations of leukocyte, fibroblast, and immune interferons, respectively. Alpha and beta interferons are usually acid-stable and correspond to what have been called Type I interferons; gamma interferons are usually acid-labile and correspond to what have been called Type II interferons. More recently, interferon tau has been described as an interferon-alpha related Type I interferon produced by bovine and ovine trophoblasts. Interferon of human and murine origin is quantified in the art in terms of International Units (IU). Interferons of other than human or murine origin can be used in accordance with this invention. In that presently accepted practices may not extend the use of "International Units" to quantify non-human and non-murine interferons, it shall be understood that administration of amounts of non-human/non-murine interferons having the same efficacy as the quantities (IU's) of human interferon specified in this description for treatment of fibromyalgia are within the scope of the present invention.

In accordance with the present invention, there is provided a method for treating fibromyalgia patients to produce a therapeutic response in said patient, said method comprising the step of administering to said patient about 1 to about 1500 IU of interferon per day, buccally, sublingually, or by oral ingestion. "Therapeutic response" as used in specifying the present invention refers to that patient response characterized by reduction in clinical symptoms of fibromyalgia in response to the treatment specified whether such improved patient condition is permanent or temporary. Buccal and sublingual administration comprises contacting the oral and pharyngeal mucosa of the patient with the dose of interferon, itself either in a pharmaceutically acceptable liquid dosage form, or in a saliva soluble dosage form which is held in the patient's mouth to form a saliva solution of the dose of interferon in contact with the oral and pharyngeal mucosa.

Interferon useful in accordance with this invention includes both Type I and Type II interferons of both heterologous or homologous origin. Preferred interferons for use in the invention include Type I interferons selected from interferon-alpha, interferon-beta and interferon-tau. The interferons can be of human or non-human origin. Methods for preparation and purification of such compositions are well-known in the art.

The clinical agent of choice for use in treatment in accordance with the present invention is human leucocyte interferon (human interferon-alpha) produced by art recognized procedures. Interferon-alpha can be mass produced by collection and purification of quantities of human buffycoat leukocytes, induction of interferon production with virus, and isolation from culture media; or interferon-alpha can be produced, for example, in accordance with the procedures described and claimed in U.S. Pat. No. 4,276,282, the disclosure which is incorporated herein by reference. Such interferon-alpha for use in accordance with this invention is commercially available. Also acceptable for use in accordance with the present invention are human interferon-alpha compositions produced by recombinant DNA technology and commercially available from Schering-Plough (Intron®), Hoffmann-LaRoche (Roferon®) and AmGen (Infergen®).

In one embodiment of this invention, the method for treating fibromyalgia comprises the step of orally administering to a patient afflicted with that disease about 0.01 to about 5.0 IU/lb patient body weight per day, more preferably about 0.25 to about 1.5 IU/lb patient body weight per day of interferon-alpha for relief of one or more symptoms of the disease. The interferon-alpha can be of heterologous (non-human) or homologous (human) origin, it can be formulated in a liquid or solid dosage form, and it can be administered by oral ingestion administration or by buccal or sublingual administration.

The interferon intended for buccal or sublingual administration in accordance with the present invention is administered to the patient in a dosage form adapted to promote contact of the administered interferon with the patients oral and pharyngeal mucosa. Thus, the dosage form can be in the form of an interferon-containing solution or syrup to be administered and used by the patient in a manner which promotes contact of the interferon component with oral mucosal tissues, for example, by holding the interferon solution in the mouth for up to one or two minutes. Preferably, the interferon for use in the present invention is formulated into a solid dosage form comprising the low dose of interferon, for example, interferon-alpha and a saliva soluble carrier optionally with desirable excipients, such as buffers, or tableting aids. The solid dosage form is formulated to dissolve, when held in a patient's mouth, to form a saliva solution of the dose of interferon to promote contact of the interferon with the oral and pharyngeal mucosa. In one embodiment, the solid dosage form is in the form of a lozenge adapted to be dissolved upon contact with saliva in the mouth, with or without the assistance of chewing, to form a saliva solution of the interferon. One preferred lozenge is formulated to provide about 0.01 to about 5.0 IU, more preferably about 0.25 to about 1.5 IU/lb of patient body weight of interferon-alpha in solution upon dissolution of the dosage form in saliva in the mouth. Lozenges for use in accordance with this invention can be prepared, for example, by art-recognized techniques for forming compressed tablets where the interferon is dispersed on a compressible solid carrier, optionally combined with any appropriate tableting aids such as a lubricant (e.g., magnesium-stearate) and compressed into tablets. The solid carrier component for such tableting formulations can be a saliva soluble solid, such as cold-water-soluble starch or a monosaccharide or disaccharide, so that the lozenge will readily dissolve in the mouth to release the contained interferon in saliva solution for contact with and absorption by the oral/pharyngeal mucosa when the lozenge is held in the mouth.

In accordance with another embodiment of the present invention an interferon pharmaceutical composition is formulated for treating patients with fibromyalgia to provide a therapeutic response. In one embodiment the pharmaceutical composition comprises about 1 to about 1500 IU of interferon-alpha in combination with a saliva soluble carrier. More preferably, the pharmaceutical composition comprises about 5 to about 1000 IU of interferon-alpha in combination with a saliva soluble carrier. Most preferably, the pharmaceutical composition comprises about 15 to about 150 IU of interferon-alpha in combination with a saliva soluble carrier.

Interferon can be administered in accordance with this invention in either a liquid (solution) or solid dosage form. Thus interferon can be administered dissolved in a buffered aqueous solution typically containing a stabilizing amount (1–5% by weight) of albumin or blood serum. Exemplary of a buffered solution suitable as a carrier of interferon administered in accordance with this invention is phosphate buffered saline prepared as follows:

A concentrated (20x) solution of phosphate buffered saline (PBS) was prepared by dissolving the following reagents in sufficient water to make 1,000 ml of solution: sodium chloride, 160 grams; potassium chloride, 4.0 grams; sodium hydrogen phosphate, 23 grams; potassium dihydrogen phosphate, 4.0 grams; and optionally phenol red powder, 0.4 grams. The solution is sterilized by autoclaving at 15 pounds pressure for 15 minutes and then diluted with additional water to a single strength concentration prior to use.

Alternatively the interferon for use in this invention by buccal, sublingual or oral ingestion administration can be formulated into flavored or unflavored solutions or syrups using a buffered aqueous solution of interferon as a base with added caloric or non-caloric sweeteners, flavor oils and pharmaceutically acceptable surfactant/dispersants. Solid dosage forms for oral ingestion administration can be prepared using standard tableting protocols and excipients to provide interferon-containing tablets, capsules, caplets, or gel seals.

Interferon in a solid dosage form can also be in the form of a lozenge adapted to be dissolved upon contact with saliva in the mouth with or without the assistance of chewing. Such a unitary dosage form is formulated to release about 1 to about 1500 IU of interferon upon dissolution in the mouth for contact with the oral and pharyngeal mucosa. Thus a unitary dosage form of interferon in accordance with this invention can be prepared by art-recognized techniques for forming compressed tablets such as chewable vitamins. Similarly, interferon can be incorporated into starch-based gel formulations to form a lozenge which will dissolve and release interferon for contact with the oral mucosa when held in the mouth. Solid unitary dosage forms of interferon for use in accordance with the present invention can be prepared utilizing art recognized dosage formulation techniques. The pH of such formulations can range from about 4 to about 8.5. Of course, in processing such unitary dosage forms one should avoid heating a pre-dosage form formulation, after addition of interferon, above about 50° Centigrade.

The daily doses of interferon-alpha for administration in accordance with this invention can be administered as single doses, or they can be divided and administered as a multiple-dose daily regimen. Further, a staggered regimen, for example, one to three days' buccal/sublingual interferon treatments per week, can be used as an alternative to daily treatment and for the purpose of defining this invention such intermittent or staggered daily regimen is considered to be equivalent to every day treatment and within the scope of this invention.

EXAMPLE 1

A Randomized, Double-Blinded, Parallel, Placebo-Controlled Study of 112 Fibromyalgia Patients Treated with Orally Administered Interferon Alpha Subjects and Methods Patients. Sequential primary fibromyalgia syndrome (FMS) patients of either sex, between the ages of 18 and 69 years were offered inclusion if they met the American College of Rheumatology [ACR] criteria for FMS diagnosis. All patients were examined to confirm the diagnosis of primary FMS and to exclude other diagnoses which might influence symptoms. Subjects were excluded for rheumatoid arthritis, systemic lupus erythematosus, chronic fatigue syndrome, untreated hypothyroidism, or prior treatment with IFN-α. The study was approved by the Institutional Review Board for human studies. Participants signed informed consent before receiving any study-related evaluations or treatment.

Medication. With only minor exceptions, all analgesic and sedative hypnotic medications typically used for the treatment of FMS were discontinued at the screening visit and proscribed for the entire duration of the study. Patients were permitted to take acetaminophen for severe headache. In addition, low-dose [85 mg/day] aspirin was allowed if previously prescribed for its anticoagulation therapy.

Enrolled patients were randomized into one of the coded study medications. Each of the study lozenges was prepared by Hayashibara Biochemical Laboratories Inc., [Okayama, Japan], and contained IFN-α at 15, 50 or 150 IU. The manufacturer also provided a placebo lozenge (0 IU) which matched the IFN-α lozenges in appearance and taste.

Administrations. Each participant was asked to dissolve one lozenge of IFN-α sublingually every morning for 6 weeks.

Outcome assessment. The participants had four clinical outcome assessments at two-week intervals over a six-week period. These were conducted without knowledge of the randomization code which was not revealed to the investigators until after the last patient completed the study and the database had been finalized. Questionnaires were used for self-assessment of symptoms and functional abilities. Tender point examinations were accomplished as previously reported (I. J. Russell, J. E. Michalek, F. MacKillip, Y. M. Lopez and G. E. Abraham, *Treatment of fibromyalgia syndrome with malic acid and magnesium: A randomized, double-blind, placebo-controlled, cross-over study;* J. Rheumatol vol. 22, pg. 953–958 (1995); A. A. Fischer, *Pressure threshold measurement for the diagnosis of myofascial pain and evaluation of treatment results,* Clin. J. Pain, vol. 2, pg. 207–214 (1987)). The Fischer pressure pain threshold algometer was used for the dolorimetry measurements (A. A. Fischer, *Pressure threshold measurement for the diagnosis of myofascial pain and evaluation of treatment results,* Clin. J. Pain, vol. 2, pg. 207–214 (1987); A. A. Fischer, *Pressure algometry over normal muscles: Standard values, validity and reproducibility of pressure threshold,* PAIN, vol.30, pg. 115–126 (1987)). The tender point examinations were systematically performed by a single individual whose FMS examination skills had been previously validated and were periodically confirmed to correspond with that of an experienced FMS investigator.

Clinical measures. The primary outcome variable was the tender point index [TPI], which is the sum of individual tenderness severities at each of the 18 standard ACR tender points. Three other variables were considered to be secondary endpoints, including the patients' self-assessment of global pain [PAIN] on a 10 cm visual analog scale [VAS], subjective assessment of physical function by VAS [FUNCTION], and the average pain threshold [APT, mean value in Kg derived from dolorimeter readings at each of the 18 ACR tender points]. Seven variables were considered to be tertiary endpoints including: the patient's VAS for headache [HEADACHE], the VAS for quality of sleep [SLEEP], the VAS for global severity of morning stiffness [STIFFNESS], the duration of morning stiffness, the Stanford Health Assessment Questionnaire [HAQ] assessment of physical function ability, the Center for Epidemiology Studies Depression Questionnaire [CESD], anxiety by the Hassles Scale [HASSLES], and the concomitant use of proscribed analgesics [ANALGESIC].

An intent-to-treat response in this study was defined as positive [agent clinically beneficial] if the patient experienced at least a 30% reduction in the TPI and no worsening with regard to PAIN, FUNCTION, or APT.

Adverse effects. Adverse clinical events reported by the patients or noted by the investigational team were recorded at the assessment visits. Laboratory tests including complete blood count, serum chemistry profile, and urinalysis were carried out on blood and urine specimens at weeks zero and four.

Sample size. Sample size needs were determined analytically. Assuming a 17% mean for non-specific improvement in the TPI among the placebo-treatment subjects in a prior study conducted by the same investigative team, it was determined that 23 evaluable patients in each group would support a 94% power for detecting a 52% average improvement (i.e. about 3-fold greater improvement than expected with placebo) in response to at least one of the IFN-α dosages. Since previous studies with FMS patients documented a 20% loss-to-follow-up, it was considered prudent to enroll 28 patients per group in order to complete the study with at least 23 evaluable patients per group.

Statistical analysis. Assessment of treatment efficacy at any evaluation visit was based on within-patient differences (changes in outcome from baseline, week zero, to the time of the evaluation visit, week two, week four, or week six). For each outcome variable, three covariates were considered: age (dichotomized at the median, 47.9 years), race (Hispanic, Non-Hispanic Caucasian, and Other), and the week zero value of the outcome variable (dichotomized on the median as Low or High) to determine whether demographically definable subgroups existed which were benefiting from the treatment.

Then, separate linear models were applied at each of the three follow-up evaluations to assess the significance of differences in outcome variable changes with time among the treatment groups [15 IU, 50 IU, 150 IU IFN-α] compared with placebo [P]. Possible adverse effects from IFN-α and the influence of resuming proscribed medications during the course of the study were assessed for statistical significance by chi-square testing. All pairwise contrasts with placebo [P vs 15 IU, P vs 50 IU, P vs 150 IU] were examined.

Results

One hundred twenty four FMS patients were screened for eligibility. Of those, 12 were not randomized because they proved not to have primary FMS [N=2], not tolerate the washout [N=21], or elected not to participate [N=8]. One hundred twelve patients qualified for study participation. They exhibited a female:male ratio of 103:9, and a mean age of 46.9 years. The ethnic distribution [Hispanic 39.3%] was slightly different than the San Antonio general population [about 60% Hispanic] because of referrals to the investigator. Twenty eight subjects were randomly assigned to each of the four treatment groups.

Table 1 summarizes the baseline values of the demographic variables at the time of study entry. Analysis of treatment groups disclosed no significant differences with regard to sex, age, or race at any visit.

Ninety nine (88.4%) of the randomized subjects completed the week two assessment, 93 (83.0%) completed week four and 90 (80.4%) (placebo, N=20; 15 IU, N=25; 50 IU, N=23; 150 IU, N=22) completed the week six evaluation Only 19.6% of the randomized patients were lost to follow-up before the end of the study, confirming the accuracy of the pre-study power calculations and the loss-to-follow-up predictions. Thus, the requirements of the sample size calculations were fully satisfied. Chi-square testing found no association between treatment group and the occurrence of protocol violations or loss to follow-up.

The treatment responses for each of the outcome measures are shown in Table 2. According to the intent-to-treat analysis, the primary variable [TPI] failed to exhibit a significant mean change from baseline to week six among all of the groups receiving IFN-α when compared with the placebo group. The same was true for the APT and subjective PAIN by VAS.

A significant improvement for global severity of morning STIFFNESS by VAS was detected for FMS subjects in the 50 IU/day (P=0.03) and the 150 IU/day (P=0.05) IFN-α treatment groups when compared with the placebo group. Pairwise treatment group contrasts for each visit showed that this change was already evident at weeks two and four. Improvement in this variable at week six for subjects receiving 50 IU of IFN-α per day was more apparent in Non-Hispanic Caucasians (mean=3.0, 95% CI=1.0, 5.1; P=0.005) than in Hispanics (mean=0.2, 95% CI=−3.6, 4.0; P=0.91) and in subjects older than the median 47.9 years (mean=3.0, 95% CI=0.5, 5.5, P=0.02) compared with the younger subgroup (mean=0.6, 95% CI=−1.8, 3.1; P=0.61).

TABLE 1

Demographic Characteristics of Subjects who Met Eligibility Criteria and were Randomized into the Study

| Variable | Placebo | IFN-α Treatment Group | | | Total |
| --- | --- | --- | --- | --- | --- |
| | | 15 IU | 50 IU | 150 IU | |
| Number | 28 | 28 | 28 | 28 | 112 |
| Age [years] | 49.5 | 47.0 | 43.7 | 47.3 | 46.9 |
| Sex [F:M] | 27:1 | 25:3 | 25:3 | 26:2 | 103:9 |
| Ethnic | C:17 | C:14 | C:19 | C:15 | C:65 |
| | H:10 | H:13 | H:8 | H:13 | H:44 |
| | O:1 | O:1 | O:1 | O:0 | O:3 |

Age:mean, C = Caucasian; H = Hispanic; O = Other Ethnic

TABLE 2

Outcomes of the Coded-Drug Study: Numbers of Subjects Competing the Study. Change in Treatment Group Sizes from Week Zero Baseline to Week Six. Values of Clinical Outcome Variables at Week Zero Baseline. Changes from Week Zero to Week Six in the Values of all Outcome Variables [Week zero minus Week six].

| Variable | | Placebo | | 15 IU | | 50 IU | | 150 IU | |
| --- | --- | --- | --- | --- | --- | --- | --- | --- | --- |
| Number | @Wk0 | 28 | | 28 | | 28 | | 28 | |
| | Chg | −8 | | −3 | | −5 | | −6 | |
| TPI | Wk0 | 31.50 | ±1.87 | 34.71 | ±1.56 | 32.32 | ±2.15 | 33.11 | ±1.93 |
| | Chg | 4.15 | ±2.85 | 1.32 | ±2.40 | 4.13 | ±1.27 | 3.82 | ±1.93 |
| Pain | Wk0 | 7.08 | ±0.37 | 6.76 | ±0.32 | 6.53 | ±0.30 | 6.61 | ±0.30 |
| | Chg | 1.37 | ±0.41 | 0.21 | ±0.36 | 0.72 | ±0.52 | 1.09 | ±0.50 |
| Funct | Wk0 | 7.68 | ±0.43 | 7.91 | ±0.38 | 7.93 | ±0.39 | 7.02 | ±0.51 |
| | Chg | 0.71 | ±0.49 | 0.73 | ±0.48 | 1.33 | ±0.63 | 0.23 | ±0.56 |
| APT | Wk0 | 2.24 | ±0.15 | 1.91 | ±0.16 | 2.21 | ±0.21 | 2.13 | ±0.18 |
| | Chg | 0.09 | ±0.21 | −0.06 | ±0.13 | 0.16 | ±0.18 | −0.07 | ±0.09 |
| Heada | Wk0 | 4.38 | ±0.59 | 4.08 | ±0.46 | 3.47 | ±0.45 | 3.86 | ±0.50 |
| | Chg | 1.39 | ±0.42 | 0.28 | ±0.60 | 0.23 | ±0.67 | 1.32 | ±0.54 |
| Sleep | Wk0 | 3.36 | ±0.42 | 3.26 | ±0.38 | 3.46 | ±0.44 | 3.58 | ±0.40 |
| | Chg | 0.90 | ±0.42 | 0.39 | ±0.34 | 0.90 | ±0.36 | 0.79 | ±0.51 |
| Stiff | Wk0 | 6.11 | ±0.52 | 7.39 | ±0.44 | 6.53 | ±0.50 | 7.13 | ±0.34 |
| | Chg | −0.54 | ±0.74 | 0.31 | ±0.59 | 1.73 | ±0.58 | 1.74 | ±0.55* |
| HAQ | Wk0 | 1.43 | ±0.11 | 1.52 | ±.12 | 1.33 | ±0.14 | 1.33 | ±0.12 |
| | Chg | −0.04 | ±0.09 | 0.08 | ±0.10 | 0.26 | ±0.08* | 0.02 | ±0.08 |
| HASSLE | Wk0 | 67.75 | ±11.89 | 70.46 | ±11.87 | 54.43 | ±8.85 | 57.86 | ±9.70 |
| | Ch | 9.05 | ±4.18 | 20.20 | ±10.18 | 9.04 | ±3.75 | 1.59 | ±6.42 |

TABLE 2-continued

Outcomes of the Coded-Drug Study: Numbers of Subjects Competing the Study.
Change in Treatment Group Sizes from Week Zero Baseline to Week Six. Values of
Clinical Outcome Variables at Week Zero Baseline. Changes from Week Zero to Week
Six in the Values of all Outcome Variables [Week zero minus Week six].

| Variable | | Placebo | | 15 IU | | 50 IU | | 150 IU | |
|---|---|---|---|---|---|---|---|---|---|
| CESD | Wk0 | 25.25 | ±2.48 | 27.82 | ±2.81 | 24.25 | ±2.88 | 26.32 | ±2.73 |
| | Chg | 1.75 | ±1.24 | 0.96 | ±1.76 | 4.74 | ±2.42 | 4.65 | ±2.06 |
| Anal [%] | Wk0 | 4 | [14.3] | 2 | [7.1] | 3 | [10.7] | 1 | [3.6] |
| | Chg | 5 | [25.0] | 0 | [0.0] | 3 | [13.0] | 1 | [4.5] |

Notes: The first row of each variable indicates the actual value from the week zero [wk0] assessment. The second row for each variable indicates the change [Chg] in variable value after six weeks of treatment. Plus means decreased and minus means increased. A higher positive value means improvement for all variables except APT and SLEEP where lower values indicate improvement. All values are expressed as mean ± SEM of the mean.
*Significant [p < 0.05].
Abbreviations: TPI = tender point index; Pain = pain by visual analog scale [VAS]; Funct-physical function; APT = average pain threshold measured by algometry; Heada = severity of headache by VAS; Sleep = quality of sleep by VAS; Stiff = morning stiffness severity by VAS; HAQ = Stanford Health Assessment Questionnaire disability score; HASSLE = Anxiety as evidenced by the Hassles scale score; CESD = Center for Epidemiologic Studies Depression scale; Anal = the use of analgesics [acetaminophen]; Wk0 = week zero baseline assessment value; Chg = change in outcome variable value from week zero to week six assessment.

At best, Non-Hispanic Caucasians (N=68) with an average baseline STIFFNESS level (mean±SDI) of 6.65±2.39 (median=6.69, range 0.0–9.9) exhibited an average improvement of 3.0 units which represents a 45% improvement over baseline. This was not a finding isolated to Non-Hispanic Caucasians with the 50 IU dosage of IFN-α, but was most dramatic with this combination of demography and dosage.

The same analytic approach detected a near-significant (P=0.06) overall improvement in physical function ability averaged over time, as assessed by the HAQ, in subjects taking 50 IU/day of IFN-α compared with placebo. A progressive trend in the direction of improvement with time was evident which finally achieved significance (mean=0.3, 95% CI=0.0, 0.6, P=0.03) at week six. Significant improvement was seen in younger patients age (age<47.9 years) (mean=0.5, 95% CI=0.0, -0.9; P=0.04) at week four and Non-Hispanic Caucasian patients (mean=0.15, 95% 0=0.1, 0.7, P=0.02) at week six.

At best, Non-Hispanic Caucasians (N=68) with an average baseline HAQ level (±SD) of 1.28±0.61, median=1.38 (range 0.0–2.63) exhibited an average improvement of 0.15 HAQ units which represents an 11.7% improvement over baseline.

All of the other secondary, and tertiary outcome variables (e.g., VAS FUNCTION, PAIN, HEADACHE, SLEEP, CESD, HASSLES, ANALGESIC) failed to show significant improvement with any dosage of IFN-α.

Adverse events present during more than one evaluation were considered to be a single event. There were 105 events reported among 65 patients, so some patients exhibited more than one. None were considered serious, nor were any of the events judged by the physician to be "related," or even "probably related" to IFN-α administration. Adverse events were quantitatively documented so they could be determined to have improved or worsened over time.

While the total numbers of individuals experiencing adverse gastrointestinal symptoms was small, patients taking the 15 IU/day IFN-α dosage were more likely to experience nausea and diarrhea than those on placebo. A borderline significant (P=0.07) change in the occurrence of diarrhea was found between the placebo-treated group (improved N=4, worsened N=0) and subjects in the 15 IU IFN-α-treated group (improved N=3, worsened N=6) between baseline and week six. Similarly, the change in the prevalence of nausea was more favorable (P=0.05) in the placebo-treated group (improved N=5, worsened N=1) than in the 15 IU IFN-α-treated group (improved N=1, worsened N=5) between baseline and week six.

The effects of treatment on clinical laboratory test values were assessed using changes in each variable from baseline to week four (i.e. changed from normal at week zero to abnormal at week four or the reverse). Matched pair analyses failed to disclose any significant change in laboratory values with treatment or by treatment group.

Discussion

Fibromyalgia syndrome [FMS] is a chronic, painful disorder commonly seen in rheumatology practice. While it is often viewed as a musculoskeletal pain process, the most prominent biological abnormalities have been found in the levels of nociceptive neurotransmitters. The etiology of FMS is not known but consideration has been given to genetic, traumatic, affective, and infectious processes as possibilities. Clinicians typically employ combinations of education, medications, exercise, rest, and psychological support; the resulting benefits are often disappointing.

In the past, there was a tendency to view FMS as a benign disorder which did not justify aggressive therapy which might carry with it any risk of adverse experience. However, that philosophy can no longer be justified considering the impact of this condition on the quality of life of affected individuals. Considering the annual cost [$16 billion in direct cost alone] of this disorder to the United States economy, innovative therapies for FMS must be considered and rigorously tested.

Interferon-α was the first cytokine to be produced by recombinant DNA technology specifically for human administration. It has emerged as an important regulator of growth and differentiation, affecting cellular communication, signal transduction and immunological regulation. In addition, Ho, et al., proposed an opioid-mediated dopaminergic mechanism for some of the effects of IFN-α (B. T. Ho, J. G. Lu, Y. Y. Hou, S. H. Fan, C. A. Meyers, L. W. Tansey, et al., *The opioid mechanism of interferon-alpha action*, ANTI-CANCER DRUGS vol. 5, pg 90–94(1994)).

All of the patients in this study met the published ACR criteria for primary FMS and exhibited its typical clinical features. Sample size calculations had predicted that if IFN-α were clinically beneficial in FMS, 23 patients should be adequate to demonstrate a significant improvement in TPI with IFN-α treatment relative to placebo treatment. That number of subjects actually did complete the week six evaluation so drop-out predictions were accurate. Therefore, the finding of no statistically significant or clinically relevant relief from deep pressure tenderness with IFN-α treatment in this study suggests that physiological dosages of IFN-α will not prove to be effective for pain relief in FMS over the short treatment interval tested.

In a companion analysis of the data in this study, the APT was found to be a slightly more reliable outcome measure than the TPI, so the APT may have been a better choice as the primary outcome variable. Indeed, a trend (non-significant) toward clinical benefit in the APT was observed with the 50 IU dosage. On the other hand, those findings were not sufficiently dramatic to change the major conclusions of the study with regard to IFN-α mono-therapy for FMS pain. Based on the effect size with APT in this study, we have estimated that reaching significance on that variable would have required each of the comparison groups to contain 2000 individuals.

This study showed that the severity of morning stiffness decreased significantly with the 50 IU/day dosage of IFN-α when compared with the placebo group. An average 45% reduction in the average severity of the morning stiffness is not trivial, especially since some subjects had much greater relief than the mean. In fact, the change in morning stiffness severity met the 30% criteria for clinically relevant improvement. By contrast, cyclobenzaprine treatment of FMS resulted in a trend toward improvement in fatigue but morning stiffness was not affected (R. M. Bennett, R. A. Gatter, S. M. Campbell, R. P. Andrews, S. R. Clark, J. A. Scarcla, *A comparison of cyclobenzaprine and placebo in the management of fibrositis: A double-blind controlled study*, ARTHRITIS RHEUM., vol. 31, pg. 1535–1542 (1988)). While improvement in physical function [HAQ] seen with IFN-α was statistically significant, it did not meet the 30% standard for clinical relevance.

With further study, IFN-α may prove to be additively or even synergistically beneficial with regard to morning stiffness when combined as adjunctive treatment with concomitant analgesic or sedative hypnotic agent therapy.

It is not clear that the slightly increased frequency of nausea and diarrhea seen with the lowest dosage of IFN-α is properly attributed to IFN-α because these side effects were not seen with the higher dosages.

It is of interest that Middleton, et al., studied 13 patients with chronic hepatitis C infection being treated with supraphysiological, pharmacological dosages (three million units three times per week) of IFN-α (G. D. Middleton, J. E. McFarlin, W. Lee, P. Lipsky Effect of alpha-interferon on pain thresholds and fibromyalgia,. ARTHRITIS RHEUM. vol. 37 [Suppl], pg. 328 (1994) (Abstract). They found that mega-dosages of IFN-α were capable of causing a generalized reduction in pain thresholds (more pain) in most patients and actually seemed to have induced fibromyalgia in some hepatitis C infected patients. If very high levels of IFN-α are capable of lower pain thresholds and inducing FMS, that may partially explain the apparent increase in the prevalence of FMS among patients with autoimmune or inflammatory diseases like RA and systemic lupus.

In sum, the study found a statistically significant improvement in one secondary and one tertiary outcome variable; an improvement in physical function assessment (HAQ) and a lessening of the severity of morning stiffness. The study failed to find a significant improvement in the primary study variable, the Tender Point Index or in two of the secondary variables, the APT and the global pain VAS. The improvement in stiffness represented a 45% reduction in morning stiffness with either 50 or 150 IU dosage levels. Though the improvement in physical function was a statistically significant improvement, it was less than the 30% improvement baseline set for clinical relevance for the study.

What is claimed:

1. A method for treating a human patient suffering from fibromyalgia to produce a therapeutic response in said patient, said method comprising the step of administering interferon buccally, sublingually, or by oral ingestion at a dose of about 1 to about 1500 IU of interferon per day, provided that the patient is not infected with hepatitis C virus.

2. The method of claim 1 wherein the interferon is administered at a dose of about 5 to about 1000 IU per day.

3. The method of claim 1 wherein the interferon is administered at a dose of about 10 to about 250 IU per day.

4. The method of claim 1 wherein the interferon is administered at a dose of about 15 to about 150 IU per day.

5. The method of claim 1, 2, 3 or 4 wherein the interferon is a Type I interferon.

6. The method of claim 5 wherein the interferon is interferon-alpha formulated in a pharmaceutically acceptable solid dosage form.

7. The method of claim 5 wherein the interferon is interferon-alpha formulated in a pharmaceutically acceptable liquid dosage form.

8. The method of claim 6 wherein the solid dosage form is a saliva-soluble solid dosage form of interferon-alpha which is administered by being introduced into the mouth of the patient and held in the mouth for a period of time sufficient to dissolve in saliva in the patient's mouth to form an interferon-containing solution.

9. The method of claim 8 wherein the solid dosage form is a lozenge.

10. A method for treating a human patient suffering from fibromyalgia to alleviate one or more clinical symptoms of that disease, said method comprising the steps of selecting a saliva-soluble lozenge dosage form of interferon-alpha, introducing the lozenge dosage form of interferon-alpha into the mouth of the patient, allowing the lozenge dosage form to dissolve in the patient's mouth to form an interferon-containing solution, and contacting the interferon-containing solution with the patient's oral and pharyngeal mucosa to stimulate a therapeutic effect, wherein the interferon-alpha is administered to the patient in an amount of about 1 to about 1500 IU interferon per day, and provided that the patient is not infected with hepatitis C virus.

11. A method for treating a human patient suffering from fibromyalgia to alleviate one or more clinical symptoms of that disease, said method comprising the step of contacting a pharmaceutically acceptable liquid formulation of interferon-alpha with the patient's oral and pharyngeal mucosa to stimulate a systemic therapeutic effect, wherein the interferon-alpha is administered to the patient in an amount of about 1 to about 1500 IU interferon per day, provided that the patient is not infected with hepatitis C virus.

* * * * *